(12) United States Patent
Roura Fernandez et al.

(10) Patent No.: US 9,649,255 B2
(45) Date of Patent: May 16, 2017

(54) CONTAINER FOR BLOOD DERIVATIVE PRODUCTS

(71) Applicant: GRIFOLS, S.A., Barcelona (ES)

(72) Inventors: Carlos Roura Fernandez, Barcelona (ES); Victor Grifols Roura, Barcelona (ES); Jordi Boira Bonhora, Barcelona (ES)

(73) Assignee: GRIFOLS, S.A., Barcelona (ES)

(*) Notice: Subject to any disclaimer, the term of this patent is extended or adjusted under 35 U.S.C. 154(b) by 11 days.

(21) Appl. No.: 14/375,542

(22) PCT Filed: Jan. 31, 2013

(86) PCT No.: PCT/ES2013/070049
§ 371 (c)(1),
(2) Date: Jul. 30, 2014

(87) PCT Pub. No.: WO2013/113967
PCT Pub. Date: Aug. 8, 2013

(65) Prior Publication Data
US 2015/0011962 A1 Jan. 8, 2015

(30) Foreign Application Priority Data
Jan. 31, 2012 (ES) .................... 201230139

(51) Int. Cl.
*A61J 1/10* (2006.01)
*A61J 1/18* (2006.01)
*A61M 1/02* (2006.01)
*G06K 7/10* (2006.01)

(52) U.S. Cl.
CPC . *A61J 1/18* (2013.01); *A61J 1/10* (2013.01); *A61M 1/02* (2013.01); *G06K 7/10366* (2013.01); *A61J 2205/60* (2013.01); *A61M 2205/60* (2013.01); *A61M 2205/6009* (2013.01)

(58) Field of Classification Search
CPC . A61J 1/10; A61J 1/18; A61J 2205/60; G06K 7/10366; A61M 1/02; A61M 2205/60; A61M 2205/6009
See application file for complete search history.

(56) References Cited

U.S. PATENT DOCUMENTS

| | | | |
|---|---|---|---|
| 6,285,285 B1 | 9/2001 | Mongrenier | |
| 7,772,981 B1 * | 8/2010 | Lambert | B65D 47/0842 340/539.1 |
| 2003/0072676 A1 * | 4/2003 | Fletcher-Haynes et al. | ... 422/23 |
| 2005/0162277 A1 * | 7/2005 | Teplitxky et al. | 340/572.8 |
| 2009/0266736 A1 * | 10/2009 | Sprishen et al. | 206/459.5 |

(Continued)

FOREIGN PATENT DOCUMENTS

WO 01/03757 A2 1/2001

OTHER PUBLICATIONS

International Search Report dated Jun. 12, 2013 for PCT/ES2013/070049.

*Primary Examiner* — Jacqueline Stephens
*Assistant Examiner* — Benjamin Klein
(74) *Attorney, Agent, or Firm* — Knobbe, Martens, Olson & Bear, LLP

(57) ABSTRACT

A hermetically-sealed plastics container for blood derivative products is provided. The container may have an internal surface and an external surface, characterized in that it comprises an RFID inlay between the internal surface and the external surface.

7 Claims, 5 Drawing Sheets

(56) References Cited

U.S. PATENT DOCUMENTS

2009/0306620 A1* 12/2009 Thilly .................. A61J 1/1412
                                                              604/415
2010/0032437 A1*  2/2010 Lossau .......................... 220/694
2010/0052859 A1*  3/2010 Lossau .......................... 340/10.1
2011/0253715 A1* 10/2011 Phaneuf et al. ............. 220/212

* cited by examiner

CONTAINER FOR BLOOD DERIVATIVE PRODUCTS

CROSS REFERENCE TO RELATED APPLICATIONS

This application is the U.S. National Phase of International Application No. PCT/ES2013/070049, filed Jan. 31, 2013, designating the U.S. and published in Spanish as WO 2013/113967 on Aug. 8, 2013 which claims the benefit of Spain Patent Application No. P201230139, filed Jan. 31, 2012.

FIELD

This invention relates to a container for blood derivative products.

In particular, this invention relates to a plasma bottle. Bottles of this type are preferably used to collect and store plasma, and in the process of thawing and emptying these bottles in the process of fractionating plasma in order to obtain blood derivative products.

It is essential that each of the units/bottles be traceable throughout the process, so that it is performed in safety, minimising risks.

In these processes full identification of the blood donor (name and identification number) is vital, as is identification of the information on the contents of each bottle, both during the collection process and during subsequent fractionating processes.

This invention supplements the PediGri® system created by Grifols in which traceability can be followed from donation to the final product.

BACKGROUND

One of the systems used at the present time uses a method of linear identification by bar codes for the information relating to each bottle of plasma used in plasma fractionating processes. However, identification by reading bar codes may give rise to limitations and defaults, and may also give rise to incorrect readings if the print quality and adhesion of the labels is not correct.

The necessity to read bar codes individually, given that a bar code has to be read on each bottle every time, is a limiting factor in some stages of the process, in that other identification systems would make it possible to increase the speed and distance at which a set of bottles is read at the same time.

There are a number of factors which can influence the print quality of the bar code, such as for example, unsuitable paper, inappropriate ribbon, inappropriate temperature (both too low and too high), the printer head pressure, the speed of printing (poorer when faster), head problems (dirt or deteriorated points) or the quality of the head (number of points which it supports; the greater the print density, the greater the need for points).

A number of defects or limitations which may be presented by bar code labels and which may result in correct reading being impossible are detailed below:

A bar code label which is scratched as a result of problems with dirt in the printer head may give rise to discontinuity in the line of bar code and prevent reading;

A mark within the bar code zone may cause the code to be read incorrectly;

Labels printed at a too high temperature (excessive density) cannot be read because of the lack of contrast between the bars and the white background;

Labels with poor print quality, when the ribbon is running out, may not be read;

Labels with a code displaced in either the horizontal and vertical axes of the label may result in the bar code being truncated, and therefore impossible to read;

Poor paper quality, together with poor ribbon quality, may result in the code being blurred;

Bar code labels for blood derivative products stored at temperatures below −30° C. may have a build-up of frosting on their surfaces, preventing them from being read;

Roughened or folded labels may not be read, or may give rise to incorrect reading;

Folded labels also cannot be read;

If the code is entered manually, there is the possibility that human error may occur as said code is being entered and a bottle's traceability is lost;

If a label is stuck on by a person, there is the possibility that two different labels may erroneously be placed on the same bottle;

A label may become unstuck either as a result of the quality of the adhesive or the surface and the temperature at which the bar code label adheres, and it will not be possible to identify a bottle;

If the type of code does not follow the ISBT standard (international standard regulating the transfer of information relating to blood transfusions), some bar code readers will not read these codes;

If any part of the label is torn, the bar code will also be illegible;

The language configuration in bar code readers may also give rise to different readings of the same code, for example, in the configuration of the Spanish keyboard the reading of the symbols equals ("=") or ampersand ("&") do not correspond to the same symbols if the reader is configured with an American keyboard; in the latter case the reader sees the symbol for an opening exclamation mark ("¡") and an oblique ("/") respectively;

Limit to the length of characters in the bar code. Different bar code readers may have different maximum character length limits, independently of the start and end of reading and check codes. Codes longer than 20 characters cannot be read in some readers;

A product may be identified by different bar coded labels which provide different information at different stages of the process and the operator must distinguish these and know which has to be read in order to correctly identify the product at each stage in the process.

Likewise the very handling of plasma bottles which have bar coded labels adhering to their surfaces may result in the bar code label becoming unserviceable once blood has been donated.

With the appearance of systems based on the emission of radiofrequency signals, such as for example, the technology of automatic radiofrequency identification or RFID, various embodiments relating to labelling with RFID inlays in containers for blood derivative products have been disclosed. The RFID technology itself makes it possible to unify the diversity of bar code labels needed for each process into a single RFID label or inlay. This makes it possible to reduce human handling and the level of human error mentioned above. Likewise, RFID technology makes it possible to store a larger quantity of information as a result of the integrated chip contained within it, allows reading, which does not have to be linear, and reading at distances greater than is possible with bar codes, making control by lots possible.

By an RFID label, RFID tag or RFID inlay is meant an assembly comprising a printed antenna or layer of conductive material capable of capturing electromagnetic waves at particular frequencies and an integrated circuit comprising a non-volatile memory in which the information is stored and which is capable of being fed by the energy originating from the electromagnetic waves.

However, location of an RFID inlay on the outside of a bottle of blood derivative products does not avoid some of the disadvantages that are present with bar codes. On the one hand, when working at temperatures below −30° C., it does not prevent such RFID inlays from accumulating frost on their surfaces, preventing them from being read. Likewise, if these RFID inlays adhere to the exterior of blood derivative products containers, there is again nothing to prevent the inlay from becoming detached or being altered or even torn off, and therefore cannot be identified.

SUMMARY

In order to overcome the problems mentioned above, this invention discloses a hermetically-sealed plastics container for blood derivative products which comprises an internal surface and an external surface. The hermetically-sealed plastics container according to this invention is characterised in that it comprises an RFID inlay between the internal surface and the external surface of the container. In this way, an integral and tamper-proof system for following and tracing blood product containers which prevents it from becoming separated from the container is obtained.

The RFID inlay may be located anywhere between the inner surface and the outer surface of the body of the container.

Thus, according to one embodiment of the invention, the RFID inlay is located in a shoulder part of the container.

According to another embodiment of the invention, the RFID inlay is located in part of a side wall of the container.

According to another embodiment of the invention, the RFID inlay is located in part of the base of the container.

According to a preferred embodiment of the invention, the RFID inlay is located within the lid of the container. In comparison with sticking an RFID inlay or bar codes to one side of the container, this embodiment prevents the RFID inlay from being folded, roughened, lost or even stolen, as it is within a lid.

In addition, as the RFID inlay is incorporated in the interior of the lid or between the two surfaces, it ensures that the inlay is better preserved and ensures that it works efficiently at a wide range of temperatures.

According to another preferred embodiment of the invention, the container comprises a moulding in the form of a tab attached to the lid in which the internal and external surfaces of the lid coincide with the internal and external surfaces of the tab.

More preferably, this tab is characterised by comprising an RFID inlay between the internal and external surfaces.

According to a preferred embodiment of the invention, the RFID inlay is of the passive UHF type and comprises a central part in the form of a coil that is open with free ends, and an integrated circuit connected to one of the ends of the coil. Preferably, this RFID inlay of the passive UHF type operates in the frequency range from 860 to 960 MHz and is suitable for both near-field communications (using the magnetic component of the electromagnetic wave) and far-field communications (using the electrical component of the electromagnetic wave).

According to another preferred embodiment of the invention, the RFID inlay is of the passive HF type and is capable of communicating preferably at a frequency of 13.56 MHz.

Preferably, the container is a plastics bottle and the blood derivative product is plasma.

A container, according to this invention, may be used to identify, follow up and trace the container at any stage from extraction of a donor's plasma to the process of fractionating the plasma to obtain blood derivative products. Likewise, the fact of being able to read RFID inlays incorporated externally in plasma containers, at a distance and automatically, makes it possible, if required, to establish control and intermediate checkpoints in that fractionation process when, for example, the containers are contained within a cage.

This invention has the potential to allow fast easy access to the processed data generated throughout the circuit from collection of the plasma in the bottle to fractionation, and facilitates the completion of documentation and the control of units required during different stages of the process, according to Good Manufacturing Practice (GMP).

For a better understanding, various figures describing the different parts of the preferred embodiments of this invention are appended by way of an explanatory but not restrictive example.

DETAILED DISCUSSION OF ILLUSTRATIVE EMBODIMENTS

Figure 1:
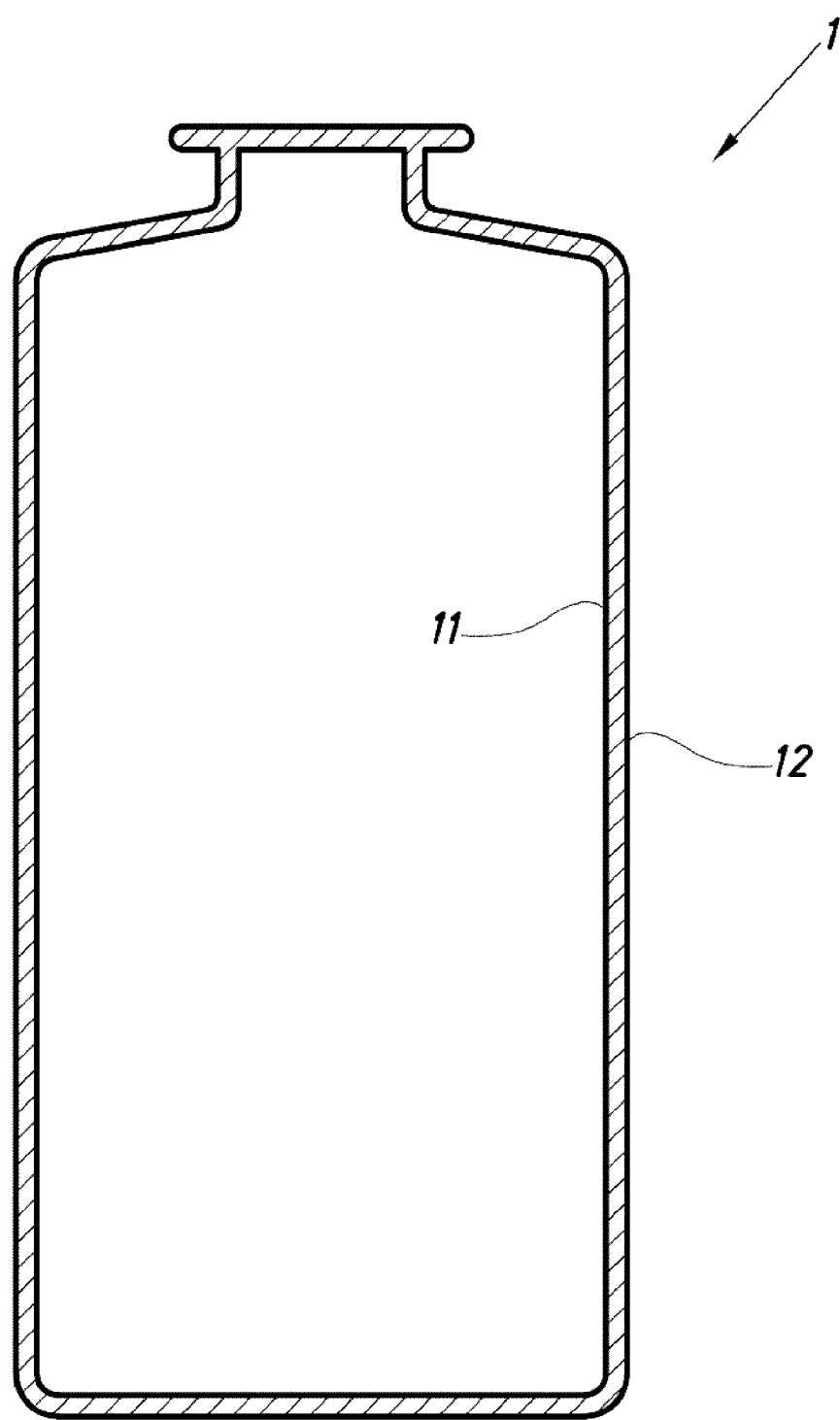
FIG. 1 shows a transverse cross-section of a container according to this invention.

FIG. 1 shows a container -1- of hermetically-sealed plastic which is preferably a plastics bottle for blood derivative products such as, for example, red blood cells, platelets or, more preferably, plasma. This container -1- is hermetically sealed and is bounded by an internal surface -11- and an external surface -12-.

Figure 5:
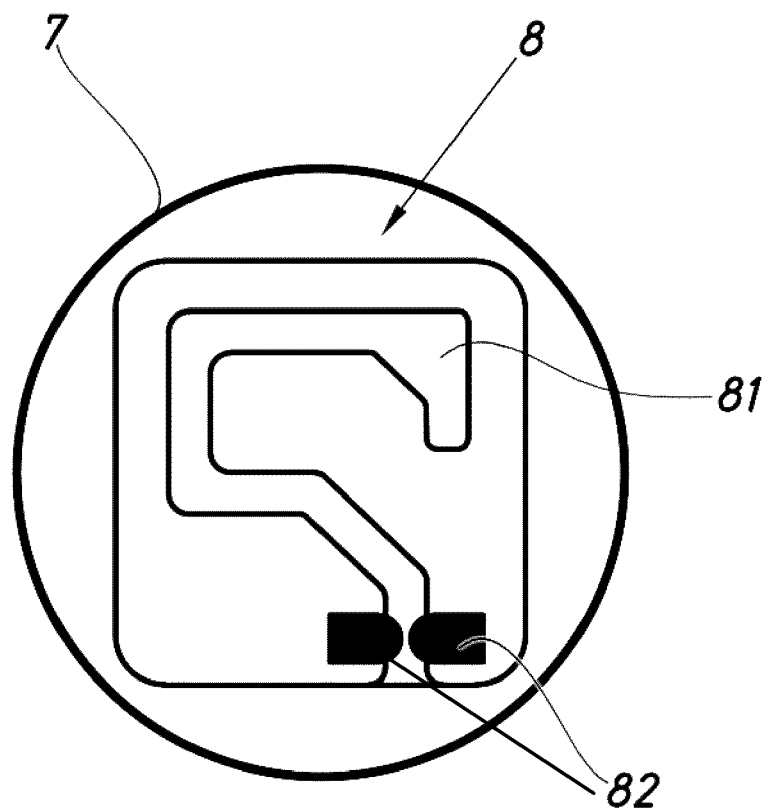
FIG. 5 shows a view from above of a lid comprising an RFID inlay for use in a container according to this invention.

According to this invention, this container -1- is characterised in that it comprises an RFID inlay -8- between internal surface -11- and external surface -12- as illustrated in FIG. 5.

According to a preferred embodiment of the invention, this RFID inlay -8- is of a type operating at Ultra High Frequency (UHF), which preferably corresponds to a range of frequencies between 840 and 960 MHz. Preferably, RFID inlay -8- according to this invention is of the UHF type and can conduct communications in both the near field (using the magnetic component of the electromagnetic wave) and the far field (using the electrical component of the electromagnetic wave). As will be seen in FIG. 5, RFID inlay -8- of the UHF type comprises an antenna element -81- in the form of an open coil with a free end in the form of a dipole and an integrated circuit -82- connected to that end. This antenna -81- is a layer of conductive material capable of capturing electromagnetic waves at specific frequencies, preferably in this case, between 840 and 960 MHz. Integrated circuit -82- is the one responsible for reading and writing data through an RFID inlay reader. Integrated circuit -82- comprises a non-volatile memory (not illustrated) in which the information is stored.

Likewise, RFID inlay -8- of the UHF type is of the passive type, that is there is no need to include a battery in the label because it obtains the power necessary to operate from the field generated by the RFID inlay interrogator or reader.

Additionally, RFID inlay -8- of the UHF type is capable of conducting optimum communications over a wide temperature range, as a result of which it is an optimal inlay for the processes of fractionating plasma bottles, through which the number of identification points can be increased and the PediGri® traceability system can be enhanced from donation through to final product.

According to another preferred embodiment of the invention, RFID inlay -8- is of the type working at high frequency (HF), that is to say at a working frequency of approximately 13.56 MHz. This type of RFID inlay -8- of the HF type is of the passive type and is capable of conducting optimum communications over a wide range of temperatures.

The container -1- according to this invention comprises an RFID inlay -8- of the passive type with the characteristics mentioned above.

Figure 2:
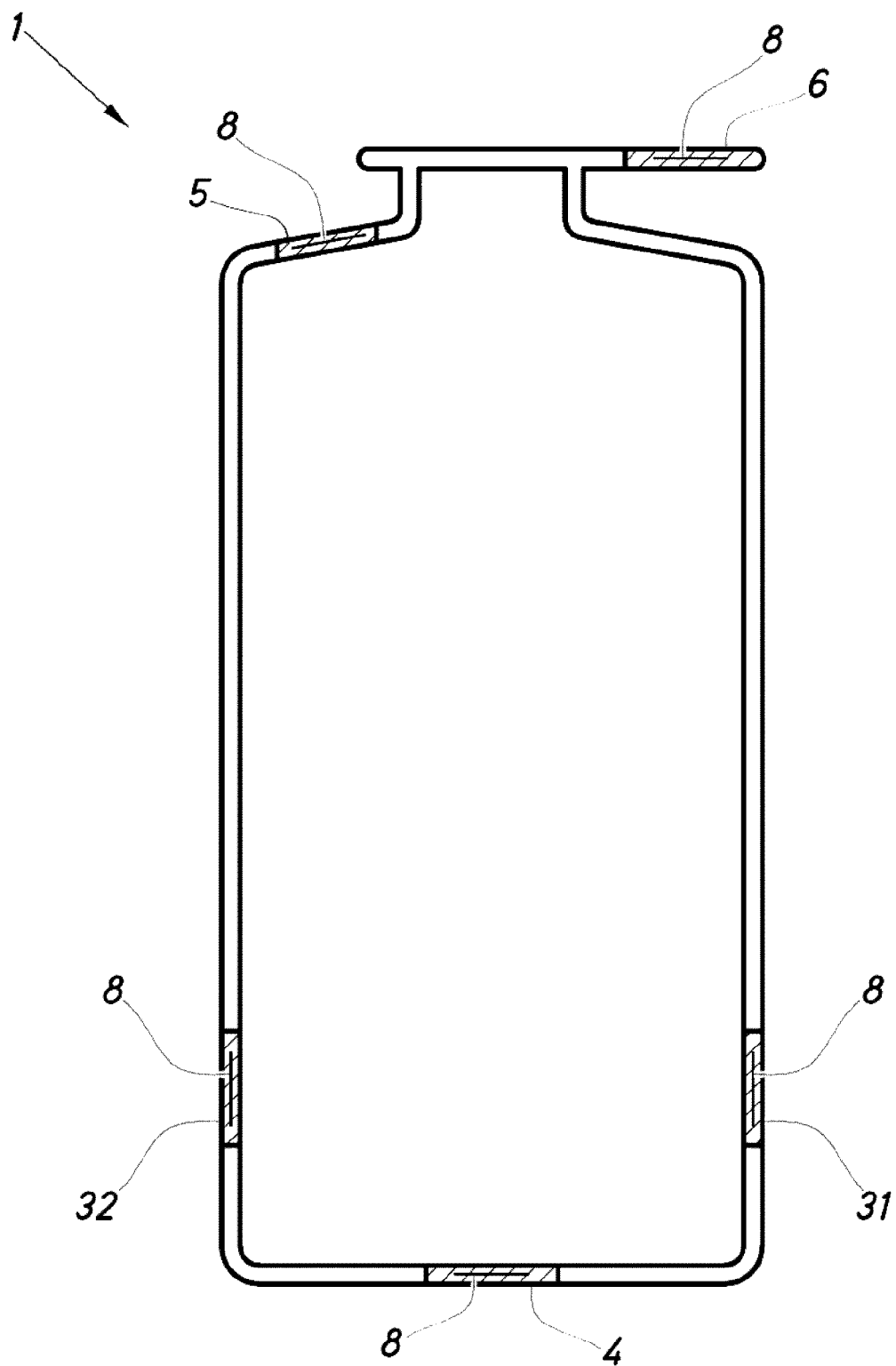
FIG. 2 shows a transverse cross-section of various embodiments of a container according to this invention.

FIG. 2 shows a container -1- which is wholly hermetically sealed by two internal and external surfaces as in FIG. 1. RFID inlay -8- may be located anywhere between the internal surface and the external surface of the body of container -1-. By the body of container -1- is meant any portion of container -1-, ignoring lid -7-, such as for example shoulder -5-, side walls -31-, -32- or base -4- of container -1-, among others. According to one embodiment of the invention, RFID inlay -8- is located in part of shoulder -5- of container -1-. According to another embodiment of the invention, RFID inlay -8- is located in part of one of the side walls -31-, -32- of container -1-. According to another embodiment of the invention, RFID inlay -8- is located in the base -4- of container -1-. According to a preferred embodiment of the invention, container -1- comprises a moulding in the form of a tab -6- attached to lid -7- of container -1- in which the internal and external surfaces of lid -7- coincide with the internal and external surfaces of tab -6-, tab -6- incorporating an RFID inlay -8- between the internal and external surfaces.

Figure 3:
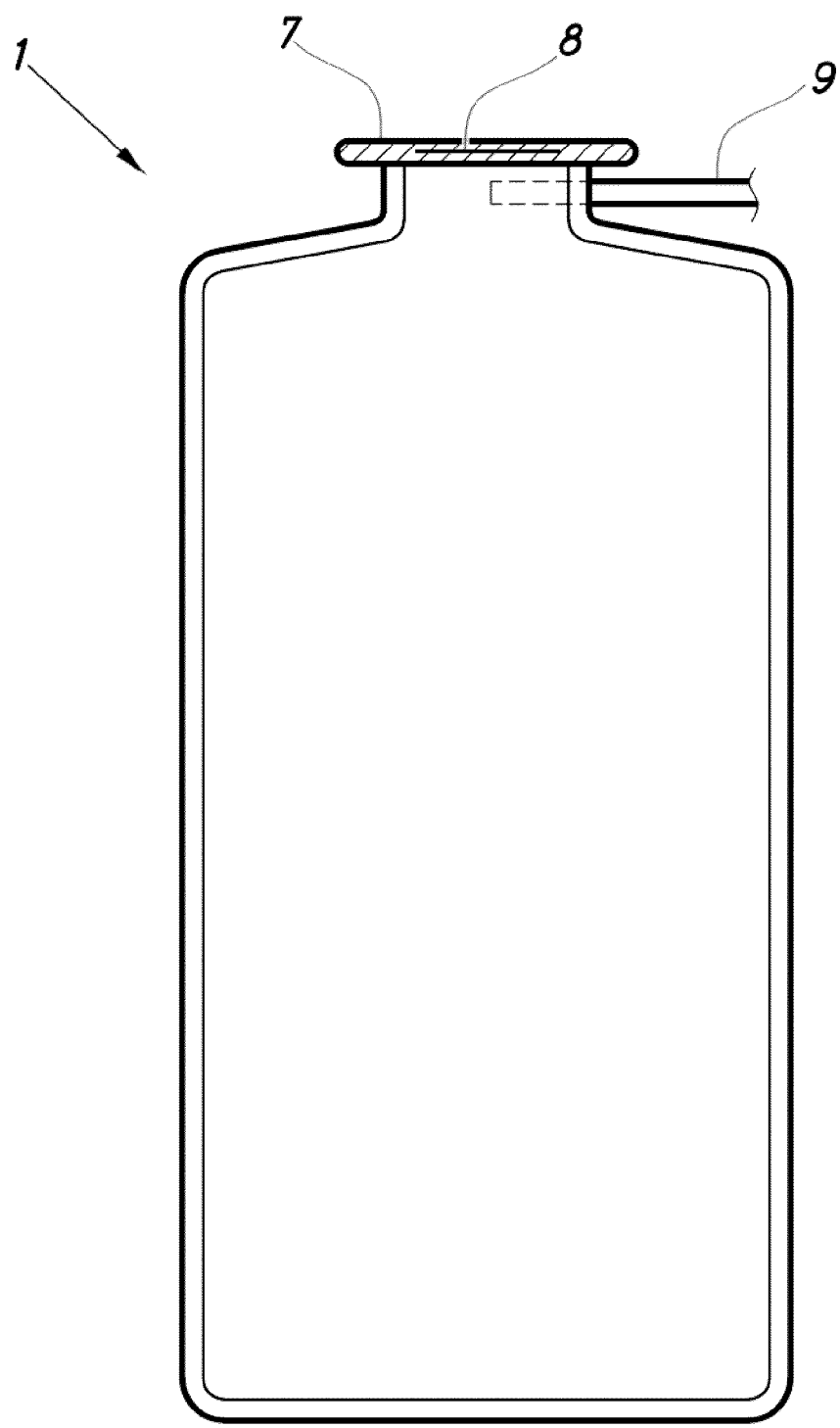
FIG. 3 shows a transverse cross-section of a preferred embodiment of a container according to this invention.
Figure 4:
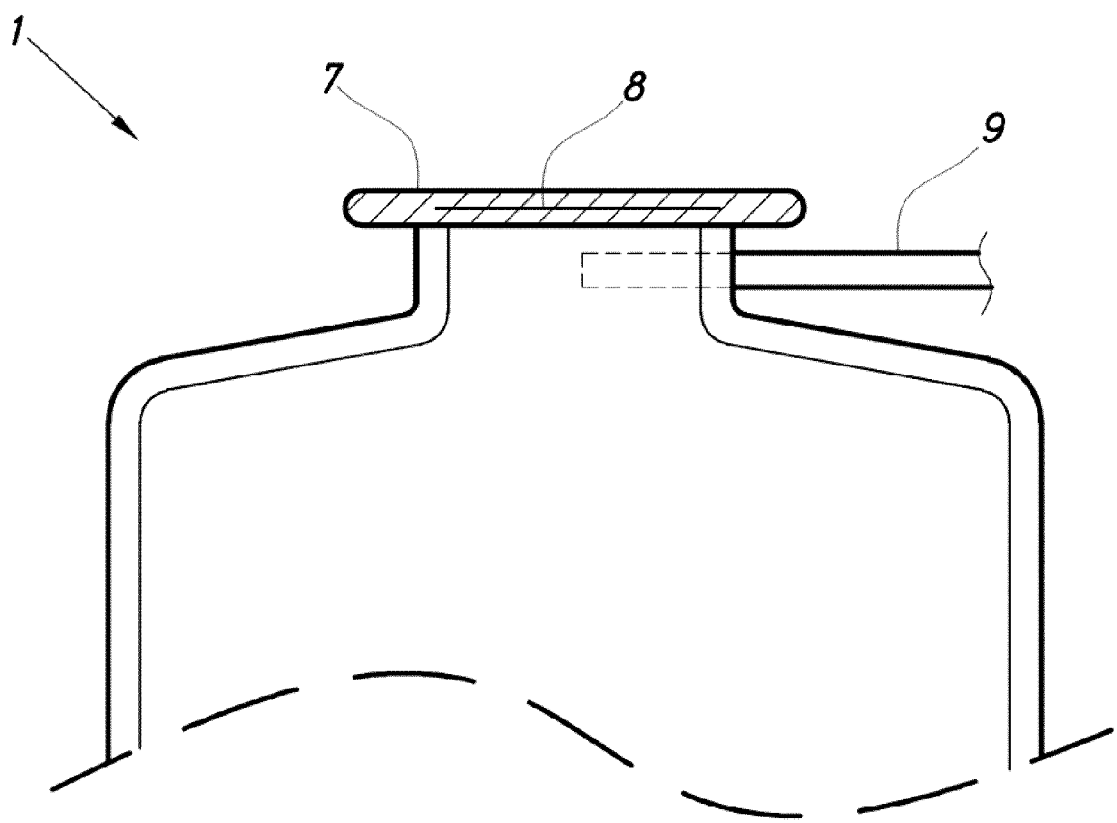
FIG. 4 shows a transverse cross-section of the top part of a container such as in FIG. 3 according to this invention.

According to a preferred embodiment of the invention and as may be seen from FIGS. 3 and 4, RFID inlay -8- is located within lid -7- of container -1-. In comparison with adhering an RFID inlay -8- or bar codes to a side of container -1-, this embodiment prevents it from being folded, roughened, lost or even stolen. In addition to this, as RFID inlay -8- is incorporated within lid -7- or between two surfaces, it ensures better preservation of RFID inlay -8- and ensures that it operates efficiently under a wide range of temperatures. A tube -9- for delivering plasma into container -1- is located in the neck of container -1- below lid -7- which includes RFID inlay -8- within it. In the normal way in processes for the collection and storage of plasma, container -1- already incorporates an RFID inlay within lid -7- and container -1- is wholly hermetically sealed.

The plasma is subsequently collected and stored within hermetically sealed container -1- through delivery tube -9- to the interior of container -1-.

In order to insert RFID inlay -8- within lid -7- of the hermetically-sealed container -1- according to this invention there are known polymer moulding processes in the state of the art such as injection moulding processes, extrusion moulding processes or moulding air blowing, among others.

Although the invention has been described in relation to preferred embodiments, these should not be regarded as limiting the invention, which is defined by the broadest interpretation of the following claims.

What is claimed is:

1. A plastic bottle for collection and storage of plasma comprising:
a container body and a lid hermetically sealed to each other to form an integral bottle,
an RFID inlay of a UHF type, and
a delivery tube extending through the container body and configured to be connected to a source of plasma so as to permit entry of the plasma into the container body,
wherein the container body and the lid of the bottle comprise an internal surface and an external surface such that they are wholly hermetically sealed other than through the delivery tube by being bounded by the internal surface and the external surface; and
the RFID inlay is sealed in the lid between the internal surface and the external surface by a molding process in a manner that prevents it from becoming separated from the container body and from the lid.

2. The plastic bottle, according to claim 1, wherein the plastic bottle comprises a molding in the form of a tab attached to the lid in which the internal and external surfaces of the container body and the lid coincide with upper and lower external surfaces of the tab and the RFID inlay of the UHF type is incorporated within the tab between its upper and lower external surfaces.

3. The plastic bottle, according to claim 1, wherein the RFID inlay of the UHF type comprises a central part in the form of an open coil with one free end forming a dipole and an integrated circuit connected to that end.

4. The plastic bottle, according to claim 1, wherein the RFID inlay of the UHF type is configured for communications in both near field and far field in a frequency range between approximately 840 and 960 MHz.

5. The plastic bottle, according to claim 1, wherein the RFID inlay of the UHF type is capable of conducting optimum communications at a temperature below −30° C. during plasma fractionating processes.

6. The plastic bottle, according to claim 1, wherein the RFID inlay is of a passive type.

7. A method for identifying, following-up and tracing a plastic bottle according to claim 1, comprising reading information associated with said RFID inlay at least once between extraction of plasma from a donor and fractionating the plasma.

* * * * *